(12) United States Patent
Cooper

(10) Patent No.: US 7,066,734 B1
(45) Date of Patent: Jun. 27, 2006

(54) CONVERTIBLE DENTAL INSTRUMENT

(76) Inventor: Ira Jeffrey Cooper, 5153 Whites La., Lexington, KY (US) 40515

( * ) Notice: Subject to any disclaimer, the term of this patent is extended or adjusted under 35 U.S.C. 154(b) by 14 days.

(21) Appl. No.: 11/036,844

(22) Filed: Jan. 14, 2005

Related U.S. Application Data

(63) Continuation of application No. 10/216,144, filed on Aug. 9, 2002, now abandoned.

(51) Int. Cl.
*A61C 1/00* (2006.01)
(52) U.S. Cl. .......................................... 433/31
(58) Field of Classification Search .................. 433/30, 433/31; 600/248; 362/138, 139, 140, 141, 362/142
See application file for complete search history.

(56) References Cited

U.S. PATENT DOCUMENTS

| | | | | |
|---|---|---|---|---|
| 300,524 A | * | 6/1884 | Starr .......................... | 362/139 |
| 341,873 A | * | 5/1886 | Bayles ........................ | 362/139 |
| 1,201,550 A | * | 10/1916 | Brush .......................... | 362/202 |
| 1,642,187 A | * | 9/1927 | Young, Jr. ................... | 600/248 |
| 1,656,754 A | * | 1/1928 | Norris ......................... | 362/139 |
| 1,712,865 A | * | 5/1929 | Allyn ........................... | 600/248 |
| 1,750,194 A | * | 3/1930 | Rydman ...................... | 362/138 |
| 1,793,463 A | * | 2/1931 | Cameron ..................... | 362/399 |
| 1,817,417 A | * | 8/1931 | Meitzler ...................... | 600/248 |
| 2,176,620 A | * | 10/1939 | Beam .......................... | 433/31 |
| 3,032,879 A | * | 5/1962 | Lafitte .......................... | 433/30 |
| 3,459,178 A | * | 8/1969 | Fleming ...................... | 600/248 |
| 4,872,838 A | * | 10/1989 | Canter et al. ................. | 433/31 |
| 4,907,135 A | * | 3/1990 | Tarrson et al. .............. | 362/109 |
| 4,993,945 A | * | 2/1991 | Kimmelman et al. ......... | 433/30 |
| 5,139,421 A | * | 8/1992 | Verderber .................... | 433/31 |
| 5,281,134 A | * | 1/1994 | Schultz ........................ | 433/29 |
| 5,348,470 A | * | 9/1994 | McGowan et al. ........... | 433/30 |
| 5,636,984 A | * | 6/1997 | Gomes ......................... | 433/30 |
| 5,741,132 A | * | 4/1998 | Usui et al. .................... | 433/30 |
| 5,915,825 A | * | 6/1999 | Weister ....................... | 362/139 |
| 6,193,386 B1 | * | 2/2001 | Reynolds .................... | 362/109 |

* cited by examiner

*Primary Examiner*—Todd E. Manahan
(74) *Attorney, Agent, or Firm*—King & Schickli, PLLC

(57) ABSTRACT

A self-contained and convertible dental instrument system includes both a lighted mirror and a direct illuminator. A hand piece has a handle section, including a battery in a housing, and a dual attachment section to receive a mirror and a light source. The illumination can be by reflection by said mirror or directly upon removal of the mirror from alignment with the light source. The handle and attachment sections preferably form a Y with the handle section reduced in size for balance and enhanced manipulation. The light source is an LED, is connected through wires in the hand piece to the battery and is controlled by a switch on the battery housing. A lens for the LED is attached by a snap-on adapter. For close contact illumination in the dental cavity, the lens includes a translucent rod, also attached by an adapter. The mirror and rod are rotatable for angular positioning to improve the illumination and the viewing.

6 Claims, 1 Drawing Sheet

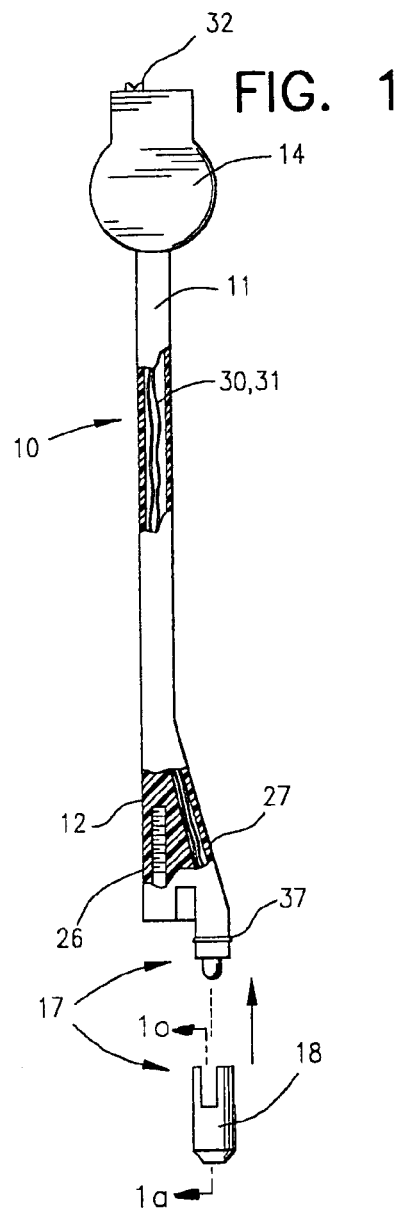
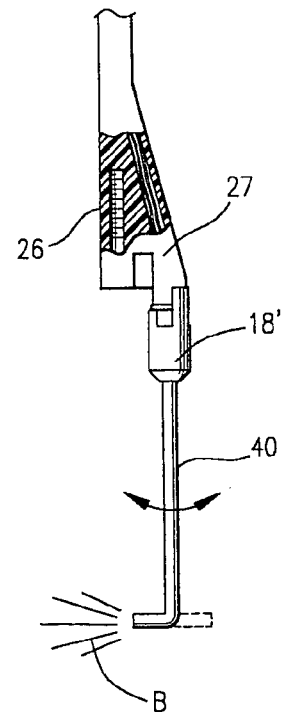
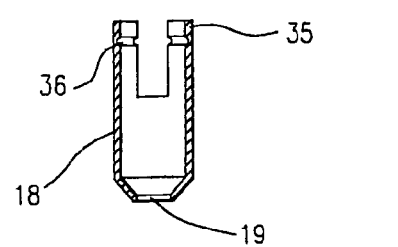
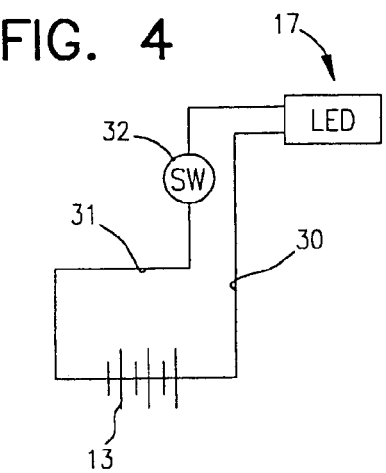
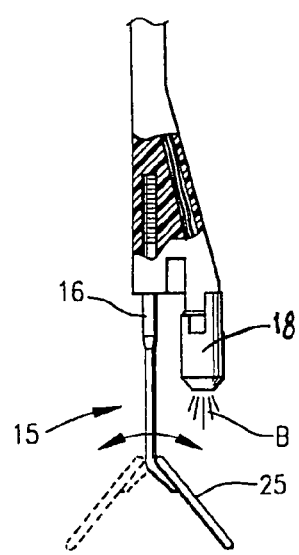

CONVERTIBLE DENTAL INSTRUMENT

This is a continuation application of U.S. patent application Ser. No. 10/216,144, filed Aug. 9, 2002 now abandoned, entitled "Convertible Dental Instrument."

BACKGROUND OF THE INVENTION

The present invention relates to dental instruments, and more particularly, to illuminated dental mirrors and related direct illuminators for the dental cavity to provide the required light for a dentist to efficiently perform work on a patient's mouth.

A dental mirror is historically the universal tool for good dentistry. It allows the dentist to see in hard to reach places in the dental or oral cavity, such as behind the teeth. This viewing is essential to a good inspection of the teeth and gums of a patient. Without it, early cavities or gum disease could be missed during a regular visit. Improvements have been made in illumination over the years, such as providing better overhead lights, but increasing illumination in the cavity is the key for even better viewing. The illumination can be used for direct viewing, or it can be associated with the mirror. It has been suggested to use a separate dedicated instrument that employs fiber optics or the like, to use in the dental cavity to back light a tooth, or a pair of teeth. In this way, light passing through the tooth, or between the teeth where cavities are prone to occur, can be extremely helpful in assuring that nothing is missed.

Heretofore, inventors have provided substantial advances in this technology. With respect to dental mirrors, the Verderber U.S. Pat. No. 5,139,421, is typical of the status of the art and the thinking in recent years. In this respect, an incandescent lamp is mounted in the handle and light is transmitted into the dental cavity through a molded translucent mirror attachment. The light is emitted in a variety of patterns, including on the mirror frame at the heel of the mirror and around the face. The objective is to vary the light emitting portions of the stem of the mirror and frame that extends out from the handle. There is more of a scattering of the light, rather than focusing of the light in areas where close up and concentrated inspection can take place. The mirror attachment in the '421 patent is also relatively expensive in that a special light transmitting plastic mirror frame and stem is required. Many dentists prefer the standard metal framed mirror that can be autoclaved for sterilization and reused.

The Usui et al U.S. Pat. No. 5,741,132, is another example of the present technology and shows an even more recent advance in the art. In this patent, the concept is to have a one way mirror so that the light can be emitted directly through the mirror from the back side. The dentist views the desired areas of the dental cavity by the reflection from the front of the mirror. Again, this invention is characterized by relatively high cost due to the special molded mirror frame; but in addition, the cost of the special one-way mirror is particularly high. Also, a general scattering type of illumination, rather than a high efficiency, focused light, appears to be the approach being taken for the actual illumination function.

Over the years, and going back even earlier, some inventors have concentrated their efforts in placing a mirror on a dental hand piece that performs many other functions, in addition to illumination. In these instruments, the hand piece is usually tethered to a fiberoptic cable that is supplied with light from a remote unit. In addition, other remote supplies, such as an air supply for drying the tooth surface, vacuum for aspirating the dental cavity and a water supply for irrigating, are all required in this type of system. In addition, the mirror and its support frame must share space on the distal end of the hand piece with other functional tools, such as retractors and the like. Representative patents teaching this approach of combining the mirror with functional tools on a tethered hand piece are Lafitte, U.S. Pat. No. 3,032,879, and Schultz U.S. Pat. No. 5,281,134.

In view of the above, it has occurred to me to take a different approach for advancing the technology in the field of illumination of the dental or oral cavity. In this respect after surveying the needs and preferences of the dentistry group of professionals, it is believed that it would be more desirable to particularly depart from the concept of adding the mirror to a tethered hand piece that performs many other non-illumination functions. At the same time, increasing the functionality and versatility of the dedicated hand piece in a system for illumination of the dental cavity should be a primary goal. To be successful in this approach to a new direction for advancing in the technology of dental mirrors, the added capability for direct illumination is important. The single instrument should be usable interchangeably to provide viewing of the teeth and gums through the mirror, or by direct viewing of the same by close contact of the illumination source, including for back lighting of the teeth. The conversion from one type of illumination to another should be accomplished quickly and easily. The hand piece should be easy to manufacture and relatively low in cost, even to the extent of being disposable, which has gained wide support in dentistry in recent years to raise sanitation levels to an even higher level.

SUMMARY OF THE INVENTION

In order to overcome the disadvantages of the prior art and meet the objectives that have been outlined, the present invention provides an instrument system that is characterized by being convertible between two modes of illumination of the dental or oral cavity of a person. In one mode, a dental mirror with a light source self-contained in a hand piece is used with the illumination preferably being focused on the mirror so that the area being viewed is fully lighted. In the second mode of operation, a translucent rod is substituted to provide a light guide, so that other areas of the cavity can be illuminated by up close contact.

The hand piece has a handle section and an attachment section. A battery is mounted directly on the hand piece and a standard mirror with a metal stem and frame is attached to a first side of the attachment section. The light source is on a second side adjacent the mirror. A lens is mounted in a removable adapter and when aligned with the mirror focuses emitted light on to the mirror. When the mirror is removed from alignment with the light beam, then the system allows for direct illumination. In this manner within the broadest aspect of the present invention, the mirror/illuminator system provides full capability for illumination regardless of the mode of operation being used. The dentist, or other dental professional, can make an easy and quick transfer from one mode of viewing to another. Rather than removing the mirror from the hand piece, the user need only rotate the mirror away from the light beam path.

Preferably, the handle section and two sides of the attachment section together form the hand piece. The handle section is the base of the Y and reduced in size relative to the two sides, which in one of the preferred embodiments takes the form of arms of the Y. The battery is mounted on the proximate end of the handle section in such a manner to offset the weight of the arms and the selected attachments during use, such as the mirror and the light source. A connector extends through the hollow center of the hand piece. Due to the balance and the relatively slim profile of the hand piece, the mirror/illuminator of the present invention provides for enhanced ease of manipulation during use. The efficiency of use is thus increased over use of other prior devices, in addition to providing increased illuminating and viewing capability.

In accordance with another feature of the present invention, the light source chosen for the instrument system is a white light emitting diode [LED]. The LED provides superior illumination in the relatively small target area, but at the same time it is efficient in terms of having a low level of current draw, has a long life, is small and light weight and relatively low in initial cost.

In the first mode of operation, an adapter with a focusing lens is attached to the first arm of the attachment section. The light can be used with the mirror when aligned to emit its beam toward the mirror, or simply as a relatively broad area illuminator when the mirror is removed or rotated out of the way. The adapter is made to snap-on by flexible prongs having a recess that mate with a rib on the mating arm.

In the second mode, a translucent plastic rod is used as the lens. The rod is mounted on an adapter that fits on the second arm in lieu of the basic lens that is used in conjunction with the mirror and for the relatively general illumination of the dental cavity. The rod provides the ability to get into close contact with the teeth and gums, such as for back lighting through individual teeth and in the gap between adjacent teeth. A lateral bend at the distal end of the rod facilitates the back lighting function and allows better, unobstructed viewing when used. The rod, like the mirror, can be rotated from side-to-side to provide the best positioning angle.

The housing and the battery at the proximate end of the hand piece counter balance the attachment section, the mirror and the light source. The micro switch that is mounted on the housing allows for easy access.

Still other objectives and advantages of the present invention will become readily apparent to those skilled in this art from the following description wherein there is shown and described a preferred embodiment of this invention, simply by way of illustration of one of the modes that is best suited to carry out the invention. As it will be realized, the invention is capable of still other different embodiments, and its several details are capable of modifications in various, obvious aspects all without departing from the invention. Accordingly, the drawings and descriptions will be regarded as illustrative in nature and not as restrictive.

BRIEF DESCRIPTION OF THE DRAWINGS

The accompanying drawings are incorporated in and forming a part of the specification, illustrate several aspects of the present invention, and together with the description serve to explain the principles of the invention. In the drawings:

FIG. 1 is a side view of the hand piece of mirror/illuminator instrument system of the present invention with parts in cross section and broken away for clarity;

FIG. 1a is a cross sectional view of the basic adapter taken along line 1a—1a in FIG. 1, and with the lens in position in the adapter;

FIG. 2 is a partial view showing the attachment section of the hand piece, with the adapter and lens attached, and the mirror in position for viewing, as well as rotated out of the way in dashed line outline form;

FIG. 3 is a partial view showing the attachment section of the hand piece, similar to the illustration in FIG. 2, but with the alternate adapter of the system having the translucent rod in place on the attachment section for close up contact illumination, and with a dashed line outline position where the rod is rotated to another position; and FIG. 4 is a schematic diagram of the electric circuit of the system.

Reference will now be made in detail to the present preferred embodiment of the invention, an example of which is illustrated in the accompanying drawings, along with the alternative embodiment.

DETAILED DESCRIPTION OF THE PREFERRED EMBODIMENT

Considering FIGS. 1, 1a and 2 of the present invention for a more detailed understanding of the specifics of the preferred embodiment, a dental hand piece 10 is shown in conjunction with the basic concept of a first mode of operation with a standard dental mirror and to broadly illuminate the dental or oral cavity of a person. The hand piece 10 has a handle section 11 and an attachment section 12. A battery 13 [see FIG. 4] is in a housing 14 on the hand piece 10. A removable mirror assembly, generally designated by the reference numeral 15, is attached by a threaded stem 16 on a first side of the attachment section 12. A light source, generally designated with the numeral 17 is on the second side of the attachment section 12. A basic adapter 18 [see enlarged view in FIG. 1a] has a lens 19 that serves to properly focus the emitted light from the light source 17. This basic combination mirror/illuminator is capable of efficiently illuminating the dental cavity in two distinct modes of operation. This objective is carried out in a manner that is highly efficient, while at the same time requiring a system that is very simple in design and construction.

With regard more particularly to the operation, it will be seen that the emitted light beam B, when used in the first mode [see FIG. 2], is directed and focused by the lens 19 toward the mirror 25 of the assembly 15. The reflection provides an excellent illumination pattern to the teeth and/or gum area that is desired to be viewed by the user. The mirror assembly 15 is preferably a standard product having a metal frame and threaded stem 16, which allows this component to be easily attached to the hand piece 10. The mirror assembly can be autoclaved and used repeatedly. As shown by the cross hatching, the hand piece is molded of plastic so that if desired, it can be considered to be disposable. The battery 13 can be particularly designed for one time use, or the housing 14 and the enclosed battery, can be made so as to be detachable and also sterilized by autoclaving.

In this preferred embodiment for illustration of the invention, the attachment section 12 is formed as a Y in conjunction with the handle section 11. In other words, the handle section 11 forms the base of the Y, and the first and second sides of the attachment section 12 forms the arms 26 and 27, respectively. In this regard, it is intended that the Y designation is a general one; it being understood that the arms 26, 27 can be positioned at any desired angle that provides a suitable separation of the attachments that are being used at the time. The handle section 11 is specifically made in a reduced diameter size compared to the attachment section 12. This allows the user to easily and comfortably grasp it during use, much like a pencil or the like, thus providing the capability for enhanced manipulation, as the viewing within the dental cavity is being made.

A connector, which is simply a pair of wires 30, 31 extends through the hollow interior of the hand piece 10. As illustrated, the light source 17 is thus connected to the battery 13 making the entire instrument system of the present invention self-contained. A switch 32 controls the on-off function of the light source. It is conveniently mounted on the housing 14 in a location separated from the side of said housing connected to the handle section 11.

The use of a white light emitting diode [LED] as the light source is found to be particularly advantageous. The light emitted from the LED is particularly good in allowing the user to see any problem areas with respect to the teeth and gums of the patient being treated. The LED requires minimum power, has a relatively long life, generates essentially no heat and is inexpensive. Thus, it provides a particularly excellent fit for the instrument system of the present invention.

As indicated above, the lens 19 that provides for the focusing of the emitted LED light, is mounted in a snap-on adapter 18. This means that the user can quickly assemble this part of the system prior to use. As shown, one preferred way of providing this feature is to incorporate flexible prongs 35 encompassing a circular recess 36 on the adapter 18. The recess 36 is designed to mate with the corresponding circular rib 37 on the second arm 27 of the attachment section 12. The adapter 18 is mounted by a simple pushing motion until the recess clicks into position on the rib 37 [see FIG. 1]. To remove the adapter 18, the reverse or simple pulling motion is used. When the adapter 18 is removed the arm 27 is ready to receive a like adapter 18' that serves to mount translucent rod 40, as will be described in detail below.

The convertible nature of the instrument system of the present invention is further enhanced by having the translucent rod 40 serve as the lens for use in close contact illumination, such as for especially high intensity spot illumination of the teeth or gums and for back lighting a single tooth or the gap between adjacent teeth. This mode of operation assures that nothing is missed and it can be used very conveniently because of the simple switching of the adapters 18,18'. An additional feature is the provision of a bend of substantially 90 degrees in the distal end of the rod 40. This facilitates placing the light emitting end in tight and hard to reach places, such as behind the teeth when back lighting is performed [see light beam B' in FIG. 3].

The stem 16 of the mirror frame fits tightly in the threaded aperture that mounts the mirror assembly 15. The positioning of the face of the mirror 25 can thus be easily adjusted by a simple rotary movement, as illustrated by the action arrow in FIG. 2. The same side-to-side adjustment can be made of the rod 40 for a better viewing angle if needed, by rotating the adapter 18' on the arm 27.

In summary, it can now be seen that a clear advantage can be gained by the dual mode operation of the dental instrument system of the present invention over the prior art arrangements. Depending on the particular need for illuminating the dental cavity to facilitate the treatment by the dental professional, the system of this invention adapts in a highly efficient manner. It provides in a single unit, the full range of capabilities that is needed for efficient lighting. It is easily convertible between a first mode of operation to provide a generally broad lighting pattern, and in conjunction with the mirror assembly 15, as illustrated with respect to FIGS. 1 and 2, and the close contact and back lighting mode utilizing the translucent rod 40, as illustrated in FIG. 3. The hand piece 10 is particularly designed for easy manipulation since the handle portion 11 is slim in relation to the attachment section 12 and is balanced with the battery housing 14. Both the mirror assembly 15 and the translucent rod may be rotated for optimum positioning. The simple design and low cost of the components of the system is particularly desirable since all or most of the hand piece 10 can be made disposable in a competitive market.

The foregoing description of a preferred embodiment of the invention has been presented for purposes of illustration and description. It is not intended to be exhaustive or to limit the invention to the precise form disclosed. Obvious modifications or variations are possible in light of the above teachings. This embodiment is chosen and described to provide the best illustration of the principles of the invention and its practical application to thereby enable one of the ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed:

1. A self-contained, convertible dental mirror and direct illuminator instrument system for viewing the dental cavity comprising:
    a hand piece having an elongated handle section and integral dual attachment section;
    a battery on said hand piece;
    a removable mirror for attachment to a first side of said attachment section, and;
    light source on a second side of said attachment section for illuminating said cavity by alignment with and reflection by said mirror, and a removable, elongated lens adapter separate from said mirror for conversion of said system for extending into said dental cavity and directly for illuminating only upon removal of said mirror from the alignment position;
    said lens adapter including a translucent rod for attachment and forming a light guide for transmitting the light into close direct contact in the dental cavity;
    whereby said mirror/illuminator system provides for a full capability of illuminating and viewing in the dental cavity.

2. The mirror/illuminator system of claim 1, said handle section forming the base of a Y on the distal end of said hand piece with said first and second sides of said attachment section forming first and second arms; said battery positioned on the proximate end of said hand piece; said handle section being reduced in size relative to said attachment section and said battery and adapted for holding substantially exclusively along said reduced handle section for balance and to allow enhanced manipulation.

3. The mirror/illuminator system of claim 2, a connector extends from said battery on the proximate end of said hand piece through and inside said handle section and directly to said second arm to said light source to provide the current to power said light source.

4. The mirror/illuminator system of claim 2, a housing is provided on the proximate end of said handle; said battery being supported in said housing for providing said balance with said attachment section; and a switch to control said light source adjacent the proximate end on said housing.

5. The mirror/illuminator system of claim 1, said light source including an LED fixed to said attachment section.

6. The mirror/illuminator system in claim 1, wherein said rod includes a lateral bend at the distal end to guide the light into direct contact in difficult to reach areas in said dental cavity.

* * * * *